US00PP09979P

United States Patent [19]

Meilland

[11] Patent Number: Plant 9,979

[45] Date of Patent: Jul. 29, 1997

[54] HYBRID TEA ROSE PLANT NAMED 'MEIROKOI'

[75] Inventor: Alain A. Meilland, Antibes, France

[73] Assignee: The Conard-Pyle Company, West Grove, Pa.

[21] Appl. No.: 662,245

[22] Filed: Jun. 14, 1996

[51] Int. Cl.[6] ..... A01H 5/00

[52] U.S. Cl. ..... Plt./11

[58] Field of Search ..... Plt./11, 16, 15, Plt./24, 22

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which abundantly and continuously forms attractive long-lasting double blossoms that are Lemon Yellow and veined and edged with a light suffusion of Poppy Red. The plant exhibits an bushy growth habit and very strong vegetation. The leaflets are glossy and contrast nicely with the bright yellow blossoms. The blossom configuration resembles that of old roses. Good disease resistance is exhibited particularly with respect to Marssonina disease. The new variety is well suited for growing as attractive ornamentation in the landscape.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the pollination of the 'Meipsilon' variety (non-patented in the United States) and the 'Landora' variety (non-patented in the United States). The male parent (i.e., the pollen parent) was 'Ausmas' variety (non-patented in the United States). The 'Landora' variety sometimes is known as the 'Sunblest' variety, and the 'Ausmas' variety has been marketed under the GRAHAM THOMAS trademark. The parentage of the new variety can be summarized as follows:

('Meipsilon'×'Landora')×'Ausmas'.

The seeds resulting from the above pollination were sown and 43 small plants were obtained which were physically and biologically different from each other. Selective study resulted in the identification of a single plant of the new variety.

It was found that the new variety of Hybrid Tea rose plant of the present invention possesses the following combination of characteristics:

(a) forms continuously and in abundance attractive double Lemon Yellow blossoms that are veined and edged with a light suffusion of Poppy Red,
(b) exhibits a bushy growth habit,
(c) is well suited for growing as attractive ornamentation in the landscape, and
(d) exhibits good disease resistance.

The new variety forms attractive blossoms that display a configuration similar to that of old roses. Particularly good resistance to Marssonina disease is exhibited.

The new variety well meets the needs of the horticultural industry and is particularly well suited for growing as an attractive display of color in the garden. The bright yellow blossoms contrast nicely with the glossy dense green foliage.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meirokoi' variety, and is marketed under the JEAN GIONO trademark.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa froebelli* understock and growing outdoors at Le Cannet des Maures, Var, France.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates two specimens of leaves with three leaflets — plan view — upper surface (left) and under surface (right); and FIG. 15 — illustrates two specimens of leaves with five leaflets — plan view — upper surface (top) and under surface (bottom).

DETAILED DESCRIPTION

Figures 1, 2, 3, 4, 5, 6, 7, 8, 9, 10, 11, 12, 13, 14, 15:
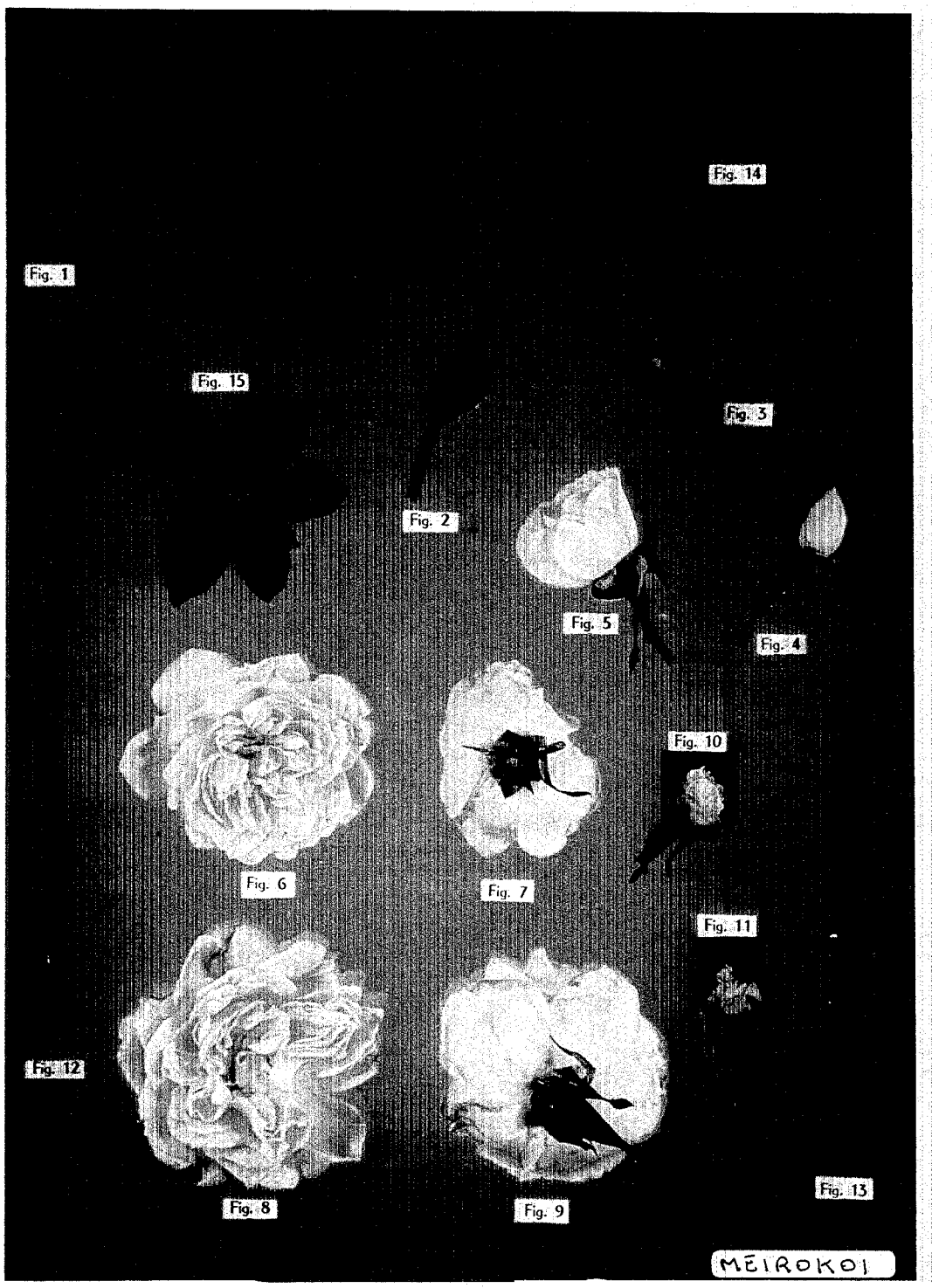

The chart used in the identification of the colors is that of The Royal Horticultural Society (R.H.S. Colour Chart). The description is based on the observation during September of two year-old plants while budded on *Rosa froebelli* understock and growing outdoors at Le Cannet des Maures, Var, France. The coloration in common terms precedes reference to the chart.

Class: Hybrid Tea.

Plant:

*Height.*—Approximately 70 to 90 cm. on average at the end of the growing season.

*Habit.*—Bushy.

Branches:

*Color.*—Young stems: light green, Green Group 143C, and more or less tinted with reddish coloration. Adult wood: medium green, Yellow-Green Group 146B.

*Thorns.*—Size: large. Quantity: very numerous (as illustrated). Color: reddish with green tip on young stems and greenish on adult wood.

Leaves:

*Stipules.*—Adnate, pectinate, very wide and linear.

*Petioles.*—Upper surface: striped reddish on young foliage and medium green on adult foliage with more or less glandular edges. Under surface: light green with some small thorns.

*Leaflets.—Number: commonly* 3, and 5 (most often). Shape: elliptic. Serration: single and regular (as illustrated). Texture: leathery. General appearance: dense and glossy foliage. Color (young foliage): Upper surface: medium green, Yellow-Green Group 146B, and more or less maculated with reddish coloration. Under surface: light green, Yellow-Green Group 146C. Color (adult foliage): Upper surface: dark green, Yellow-Green Group 147A. Under surface: light green, Yellow-Green Group 143C.

Inflorescence:

*Number of flowers.*—Usually one to three flowers per stem.

*Peduncle.*—Light green in coloration with more or less glandular edges. The length is approximately 3.5 to 4 cm. on average.

*Sepals.*—Upper surface: tomentose, and greenish in coloration. Under surface: light green in coloration and sometimes possess appendiculated and glandular edges.

*Buds.*—Shape: globular. Length: approximately 2 to 2.5 cm. on average. Size: large. Color upon opening: Upper surface: Lemon Yellow, Yellow Group 13B. Under surface: light Lemon Yellow, Yellow Group 13C, with Canary Yellow, Yellow Group 9A at the base.

*Flower.*—Shape: similar to that of old roses (as illustrated). Diameter: approximately 9 to 10 cm. on average. Color (when opening begins): Upper surface: Lemon Yellow, Yellow Group 13B, and veined and edged with a light suffusion of Poppy Red, Red Group 40D, becoming lighter on the outer petals. Under surface: light Lemon Yellow, Yellow Group 13C, and veined and edged with a light suffusion of Poppy Red, Red Group 40D, becoming lighter on the outer petals. Color (when blooming): Upper surface: Lemon Yellow, Yellow Group 13B, and veined and edged with a light suffusion of Poppy Red, Red Group 40D, becoming lighter on the outer petals. Under surface: light Lemon Yellow, Yellow Group 13C, and veined and edged with a light suffusion of Poppy Red, Red Group 40D, becoming lighter on the outer petals. Color (at end of opening): Upper surface: Lemon Yellow, Yellow Group 13B, and veined and edged with a light suffusion of Poppy Red, Red Group 40D, becoming lighter on the outer petals. Under surface: light Lemon Yellow, Yellow Group 13C, and veined and edged with a light suffusion of Poppy Red, Red Group 40D, becoming lighter on the outer petals. Fragrance: none. Lasting quality: very long. The blossoms commonly last approximately 7 to 10 days when present on the plant. The blossom life is influenced by the environmental conditions that are encountered. Petal drop: good. Petal shape: the outer petals are rounded with a cuneate base and an indented tip, and the inner petals are oval and become very thin near the center of the receptacle. Petal number: approximately 110 to 120 on average. Stamen number: approximately 30 to 35 on average. Anthers: typical, large, and golden yellow in coloration. Filaments: typical, bright yellow in coloration. Pistils: approximately 120 to 125 on average. Stigmas: typical and sometimes display a vegetative center. Styles: greenish in coloration and commonly possess a fuchsine tip. Receptacle: medium green in coloration, smooth, and in longitudinal section in the shape of a large pitcher.

Development:

*Vegetation.*—Very strong.

*Blooming.*—Continuous and very abundant.

*Aptitude to bear fruit.*—Good.

*Resistance to diseases.*—Good with particularly good resistance to Marssonina disease being exhibited.

I claim:

1. A new and distinct variety of Hybrid Tea rose plant characterized by the following combination of characteristics:

(a) forms continuously and in abundance attractive double Lemon Yellow blossoms that are veined and edged with a light suffusion of Poppy Red,
(b) exhibits a bushy growth habit,
(c) is well suited for growing as attractive ornamentation in the landscape, and
(d) exhibits good disease resistance;

substantially as herein shown and described.

* * * * *

MEIROKOI